United States Patent [19]
Rydell

[11] Patent Number: 5,269,754
[45] Date of Patent: Dec. 14, 1993

[54] LAPAROSCOPIC CHOLANGIOGRAM DEVICE

[75] Inventor: Mark A. Rydell, Golden Valley, Minn.

[73] Assignee: Everest Medical Corporation, Minneapolis, Minn.

[21] Appl. No.: 830,200

[22] Filed: Jan. 31, 1992

[51] Int. Cl.$^5$ ............................................. A61M 31/00
[52] U.S. Cl. ..................... 604/52; 604/159; 604/164; 604/166; 604/174; 604/178; 604/264; 604/272; 606/167
[58] Field of Search ............... 606/167, 181, 184, 185; 604/21, 52, 158, 159, 164, 165, 166, 167, 174, 178, 181, 272, 264, 268

[56] References Cited

U.S. PATENT DOCUMENTS

| | | | |
|---|---|---|---|
| 3,122,138 | 2/1964 | Geary | 604/115 |
| 3,727,613 | 4/1973 | Sorenson et al. | 604/165 |
| 4,222,380 | 9/1980 | Terayama | 604/115 |
| 4,299,219 | 11/1981 | Norris, Jr. | 604/115 |
| 4,393,870 | 7/1983 | Wagner | 604/115 |
| 4,693,257 | 9/1987 | Markham | 604/167 |
| 4,763,667 | 8/1988 | Manzo | 604/173 |
| 5,071,412 | 12/1991 | Noda | 604/268 |
| 5,139,487 | 8/1992 | Baber | 604/165 |
| 5,176,647 | 1/1993 | Knoepfler | 604/181 |

FOREIGN PATENT DOCUMENTS

| | | | |
|---|---|---|---|
| 2230632 | 1/1973 | Fed. Rep. of Germany | 604/272 |
| 1121013 | 10/1984 | U.S.S.R. | 604/264 |

Primary Examiner—Stephen C. Pellegrino
Assistant Examiner—Jeffrey A. Schmidt
Attorney, Agent, or Firm—Haugen and Nikolai

[57] ABSTRACT

A surgical instrument for facilitating the injection of a contrast fluid into the cystic duct during the course of a laparoscopic cholecystectomy procedure comprises an elongated, rigid outer tubular member whose outer diameter permits it to pass through the lumen of a trocar penetrating the patient's abdominal wall and of a length allowing the distal end of the instrument to abut the patient's cystic duct. Affixed to the proximal end of the outer tubular shaft is a grip that includes a plunger which can be reciprocally moved in the longitudinal direction and joined to the plunger is an inner tube which can be joined at its proximal end to a source of contrast fluid and which extends through the lumen of the outer tubular shaft. Affixed to the distal end of the inner tube is a hollow hook-shaped needle which is in fluid communication with the lumen of the inner tube and which has a sharpened distal end for piercing through the wall of the cystic duct when the plunger is depressed to thereby hook and hold the instrument with the open end of the needle in the cystic duct. By injecting contrast fluid into the proximal end of the instrument, it flows through the inner tubular member and the hollow needle into the cystic duct.

8 Claims, 1 Drawing Sheet

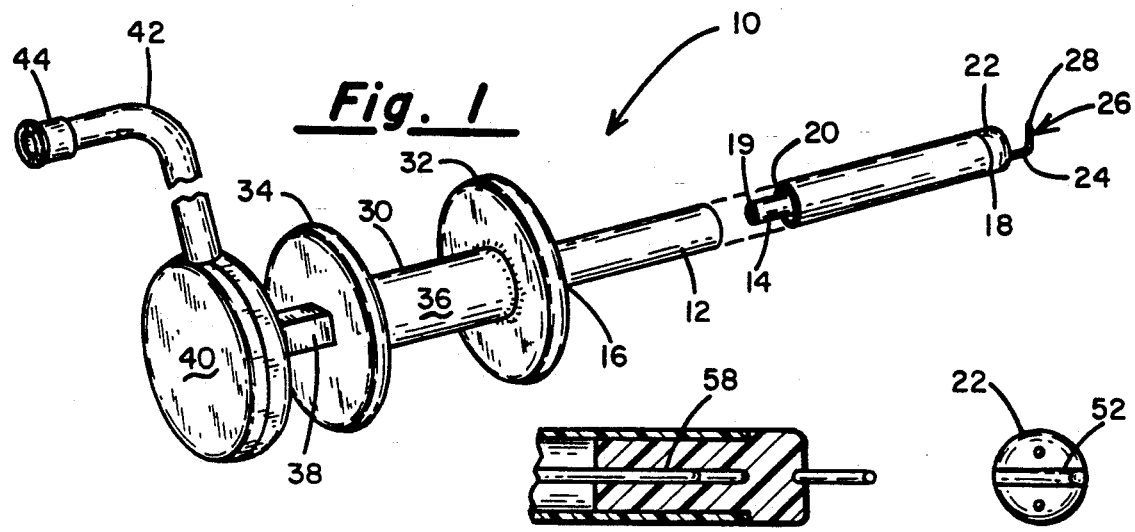
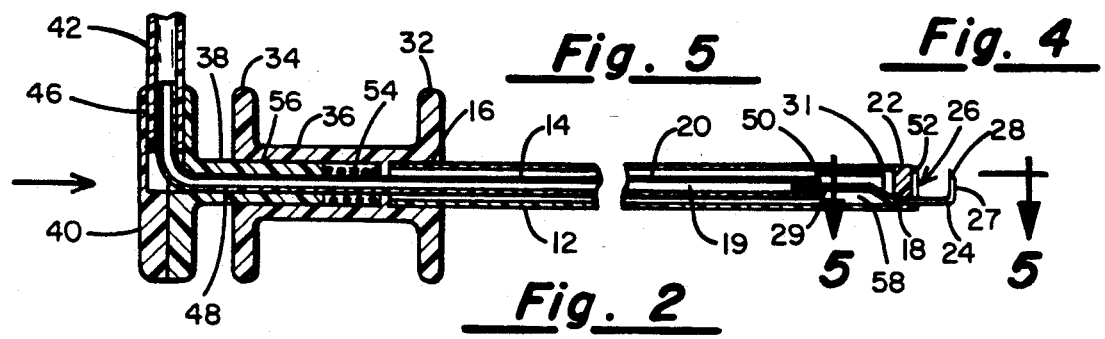

LAPAROSCOPIC CHOLANGIOGRAM DEVICE

BACKGROUND OF THE INVENTION

I. Field of the Invention

This invention relates generally to instruments to be used during the performance of a laparoscopic cholecystectomy procedure, and more particularly to an instrument for carrying out a laparoscopic cholangiogram.

II. Discussion of the Prior Art

Fairly recently, with the introduction of improved laparoscopes, allowing the viewing of a surgical site on video screens, and the development of improved dissecting instruments, including electrocautery and laser instruments, laparoscopy has become a more popular procedure. Rather than making a long incision through the abdominal wall, surgical operations are conducted through small puncture sites in the anterior abdominal wall. Surgeons have used laparoscopic techniques to evaluate tumors, lyse adhesions and conduct biopsies on internal organs. Because the laparoscopy obviates the need for large incisions made through the abdominal muscles, procedures that once required hospitalization for a week or more can now be performed on an outpatient basis.

Relatively recently, laparoscopy has been used in performing cholecystectomy surgery. Here, a video guidance tube is inserted through an incision in the navel and the gallbladder is removed through three other tiny incisions made in the upper abdomen. More particularly, in carrying out such surgery, a small 2-3 cm skin incision is placed just below the umbilicus to allow passage of a 11 mm trocar that will house the diagnostic laparoscope. This site is ideal because the peritoneum is firmly attached to the fascia and skin. Hence, it is less likely that a properitoneal insufflation will take place.

Next, a Veress needle is passed through the abdominal wall and used to insufflate the abdomen with $CO_2$. This gas is introduced to a pressure of about 14 mm Hg which distends the abdomen and increases the surgical working space. Once the 11 mm trocar is introduced, the diagnostic laparoscope is placed and the additional puncture sites are made under direct vision while looking at a video monitor. The additional puncture sites allow grasping tools and dissection instruments to be inserted into the abdominal cavity.

Before the gallbladder is excised, it is good practice to do a cholangiogram to exclude the presence of choledocholithiasis so that an endoscopic retrograde cholangiopancreatography with sphincterotomy and stone extraction can take place before the laparoscopic cholecystectomy procedure continues.

In accordance with the prior art, a cut is made through the wall of the cystic duct, followed by the insertion of an ovarian aspiration needle through that incision and the injection of a contrast fluid, such as HYPAQUE ®, through that needle and into the duct. Once the cystic duct and surrounding anatomy has been explored fluoroscopically, the dissection of the cystic duct, the cystic artery and the gallbladder itself can proceed.

The present invention is concerned with an improved instrument for performing a laparoscopic cholangiogram and it has the advantage of not requiring plural instrument exchanges to accomplish the procedure. Rather than using a scalpel, scissors or other instrument to first cut into the cystic duct and then replacing the cutting instrument with an ovarian needle as in the prior art, the instrument of the present invention is capable of being clamped at its distal end to the exterior wall of the cystic duct with a needle-like probe penetrating through the wall for allowing the radiopaque fluid to be injected therein. It remains secure until the cholangiogram has been completed and obviates the somewhat difficult procedure of locating a previously made incision with the distal end of an ovarian needle. Moreover, the prior art ovarian needle is not self-anchoring and, as a result, it can lose its purchase relative to the small incision that had been made in a cystic duct.

OBJECTS

It is accordingly a principal object of the present invention to provide an improved device for carrying out a laparoscopic cholangiogram.

Another object of the invention is to provide an instrument which is dimensioned to fit through a trocar or through an abdominal puncture so as to reach the cystic duct, and which then clamps to the cystic duct with a hollow needle probe penetrating the wall thereof for allowing a contrast fluid to be injected.

Another object of the invention is to provide a laparoscopic cholangiogram instrument having a needle-like probe which is generally shielded while the instrument is being inserted through the abdominal wall and which can be extended to penetrate the wall of the cystic duct by simple manipulation of a plunger located at the proximal end of the instrument.

SUMMARY OF THE INVENTION

The present invention relates to a new and improved surgical instrument for performing a laparoscopic cholangiogram. It comprises an elongated outer tubular member dimensioned to fit through a trocar insertable through the abdominal wall of a patient. An inner tubular member is coaxially disposed within the lumen of the outer member and extends from the proximal end of the outer member toward, but short of, the distal end thereof. The inner tubular member is reciprocally movable between first and second positions. A rigid hollow needle having a beveled distal tip defining a sharp point is sealingly joined to the distal end of the inner tubular member, with the needle being shielded when the inner tubular member is in the first position but is exposed when the inner tubular member is in its second position.

Affixed to the proximal end of the outer tubular member is a grip, and that grip includes a longitudinal bore which receives a spring-biased plunger whose proximal end is outside of the grip and adapted to be manipulated by the surgeon's thumb. The distal end of the plunger is secured to the inner tubular muscle and, as such, manipulation of the plunger is used to extend and retract the hollow needle relative to the distal end portion of the outer tube. The needle is preferably bent at a predetermined angle relative to the longitudinal axis of the instrument so that when the plunger is depressed, the needle can puncture the wall of the cystic duct, but when the plunger is released, the spring bias causes the wall of the cystic duct to be pinched or clamped between the needle probe and the distal tip of the outer tubular member, holding the instrument in place.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts.

FIG. 1 is a perspective view of the instrument of the present invention;

FIG. 2 is a longitudinal cross-sectional view of the instrument of FIG. 1 with the plunger depressed to expose the needle probe;

FIG. 3 is a longitudinal cross-sectional view of the instrument of FIG. 1 when the plunger is retracted and the needle probe shielded;

FIG. 4 is an end view of the instrument of FIG. 1 with the penetrating needle not shown;

FIG. 5 is a cross-sectional view taken along the line 5—5 in FIG. 2;

FIG. 6 is a partial perspective view of the distal end portion of the instrument of FIG. 1; and FIG. 7 is a greatly enlarged view showing the manner in which the instrument of the present invention engages the cystic duct at the time that the radiopaque dye is injected.

DESCRIPTION OF THE PREFERRED EMBODIMENT

The laparoscopic cholangiogram instrument is indicated generally by numeral 10 in the perspective view of FIG. 1 and is seen to comprise an elongated rigid outer tubular member 12 which, typically, may be about 12–15 in. in length and which surrounds a coaxially disposed inner tubular member 14. The outer tube 12 may be a stainless steel tube having an O.D. of about 0.205 in. It has a proximal end 16 and a distal end 18 and a lumen 20 extending therebetween. Inserted into the distal end 18 of the outer tube is a plug 22 having a slotted bore formed therethrough for accommodating a first straight, longitudinally directed shank portion 24 of a rigid hollow tubular needle indicated generally by numeral 26. The needle 26 has a transversely bent section 27 terminating in a beveled distal end 28 creating a sharpened point. The needle 26 may be formed from hypodermic stock and it has been found that a 20 gauge needle has a sufficiently large bore to permit radiopaque contrast fluid to flow therethrough and out the opening of the beveled tip 28.

Affixed to the proximal end 16 of the instrument 10 is a grip 30 which is spool-shaped with radially projecting flanges 32 and 34 spaced from one another by a central cylindrical segment 36. This configuration conveniently allows the forefinger and index finger of one hand to fit between the flanges.

As will be further explained hereinbelow, a longitudinal bore passes through the grip 30 and is preferably of a non-circular cross-section, e.g., square, for receiving a complimentary shaped plunger shaft 38 therein. Affixed to the proximal end of the shaft 38 is a thumb pad 40. Extending through a radial port in the thumb pad 40 and communicating with a bore formed centrally through the shaft 38 is a short length of flexible plastic tubing 42 which terminates in a luer lock fitting 44 to which a pressurized source of radiopaque contrast fluid (not shown) can be connected.

Having described the exterior features of the device with the aid of FIG. 1, consideration will next be given to its interior construction and, in this regard, reference is made to the cross-sectional views of FIGS. 2 and 3. As can be seen from these figures, the flexible plastic tube 42 fits into a radial bore 46 formed in the thumb pad member 40 and inserted into the end of the tube 46 is the proximal end of the inner tubular member 14, the tube being bonded in fluid-tight engagement. The inner tubular member 14 may comprise a HYTREL® tube having a 0.090 in. O.D. and a 0.070 in. I.D. It extends through a longitudinal bore 48 formed in the stem 38 of the plunger and through the lumen 20 of the outer tubular member 12 to its distal end 50. Sealed in the distal end 50 of the inner tube 14 is the proximal end of the rigid hollow needle 26. As such, radiopaque contrast fluid injected through the luer fitting 44 and the tube 42 will flow through the inner tube 14 and through the lumen of the hollow needle 26 to exit the opening in the beveled tip 28.

Referring to FIG. 4 which shows a distal end view of the instrument, it can be seen that the plug 22 contains a diametrically directed slot or groove 52 into which the transversely directed portion 27 of the needle 26 may fit when the plunger 40 is not being depressed. Thus, the sharp tip 28 of the needle is effectively shielded until such time as the plunger 40 is depressed.

As can best be seen in FIGS. 2 and 3, there is contained within the grip 36 a compression spring 54 which cooperates with the plunger shaft 38 and the grip 36 to normally urge the plunger to its extended position as shown in FIG. 3. When in this position, the transversely bent portion 27 of the hollow needle 26 fits into the groove 52 in the tip member 22 and is thus shielded from engaging tissue until it is actually deployed.

As was mentioned in connection with FIG. 1, the shaft 38 is preferably non-circular and cooperates with a similarly shaped bore 56 formed in the grip 36 so as to prevent relative rotation between these two parts. Moreover, as is visible in FIGS. 2, 3 and 5, the tip member 22 has a longitudinal slot 58 formed therein for receiving the two longitudinally offset proximal portions 29 and 31 of the hollow needle 26. Because the length of the offset exceeds the width of the slot 58, the needle 26 is constrained against rotation as well.

FIG. 6 illustrates a partial perspective view of the distal end portion of the instrument of FIG. 1 with the plunger 40 depressed to extend the needle 26 distally of its groove 52. This view also reveals a pair of optional, longitudinally projecting pins 60 and 62 which are bonded in place in bores formed in the distal end surface of the plug 22. In use, the instrument described is passed through a trocar or directly through a small puncture made in the abdominal wall until the distal end of the instrument is touching or closely adjacent the wall of the cystic duct identified by numeral 64 in FIG. 7. Now, when plunger 40 is depressed, the rigid hollow needle 26 can be made to penetrate completely through the wall 64 into the duct's lumen while the pins 60 and 62 engage the tissue of the wall. Upon subsequent release of the plunger 40, the spring 54 serves to squeeze the vessel wall 64 between the transversely bent portion 27 of the needle 26 and the end surface of the plug member 22 with the pin points 60 and 62 penetrating into the wall of the duct to firmly clamp the instrument to the vessel wall. Contrast fluid is then made to flow through the inner tube 14 and out the beveled tip 28 of the hollow needle 26 into the lumen of the duct.

It is recognized that the terminal portion of needle 26 may be shaped or bent in a way to enhance penetration of the wall of the duct as the plunger is depressed once the tip end of the instrument is against the duct's wall but with the ability to tip the instrument at an angle to the wall, little difficulty is encountered in making the needle 26 illustrated enter through the duct wall.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A surgical instrument for performing a laparoscopic cholangiogram comprising:
   (a) an elongated outer tubular member dimensioned to fit through a trocar insertable through the abdominal wall of a patient, said outer tubular member having a proximal end, a distal end and a lumen extending therebetween;
   (b) an inner tubular member coaxially disposed within said outer tubular member and extending from said proximal end toward, but short of, said distal end of said outer tubular member and reciprocally movable therein between first and second positions, said inner tubular member also having a proximal end, a distal end and a lumen extending therebetween; and
   (c) a rigid hollow needle having first and second longitudinal segments integrally joined by an offset segment, a distal end portion of said rigid hollow needle bent at a predetermined angle relative to said second longitudinal segment, and a beveled distal tip defining a sharp point, said needle having a proximal end sealingly joined to said distal end of said inner tubular member, said distal tip of said needle being shielded when said inner tubular member is in said first position and exposed when in said second position; and
   (d) a plug member inserted into said distal end of said outer tubular member and having a slot receiving said offset segment therein and being more narrow in width than the length of said offset segment for precluding rotation of said rigid hollow needle relative to said outer tubular member.

2. The surgical instrument as in claim 1 and further including:
   (a) a grip attached to said proximal end of said outer tubular member; and
   (b) a plunger mounted for reciprocating movement within said grip, said plunger being joined to said inner tubular member.

3. The surgical instrument as in claim 2 wherein said grip and said plunger each include a longitudinal bore through which said inner tubular member passes.

4. The surgical instrument as in claim 2 and further including means for resiliently biasing said plunger relative to said grip in a direction to position said inner tubular member in said first position.

5. The surgical instrument as in claim 1 and further including means for injecting a radiopaque contrast fluid into said proximal end of said inner tubular member.

6. The surgical instrument as in claim 1 wherein said plug member includes a groove for receiving said distal end portion of said hollow needle when said inner tubular member is in said first position.

7. A method for performing a laparoscopic cholangiogram procedure comprising the steps of:
   (a) inserting a trocar through the abdominal wall of a patient;
   (b) inserting an elongated tubular member having a reciprocally displaceable inner tubular member coaxially disposed therein with a hook-shaped hollow needle secured to the distal end of said inner tubular member, through said trocar;
   (c) hooking said elongated tubular member to the patient's cystic duct by inserting said hook-shaped hollow needle through the wall of said duct, and retracting said hook-shaped hollow needle against the inside wall of said duct; and
   (d) injecting a contrast fluid through said inner tubular member and said hollow needle into the cystic duct.

8. A method for performing a laparoscopic cholangiogram procedure comprising the steps of:
   (a) inserting a trocar through the abdominal wall of a patient;
   (b) inserting an elongated tubular shaft having a finger grip affixed to a proximal end of said shaft and a spring-loaded plunger reciprocally movable within said grip, with the plunger being affixed to an inner tubular member coaxially disposed within the lumen of said tubular shaft, and a hook-shaped hollow needle connected in fluid communication with said inner tubular member through said trocar;
   (c) bringing the distal end of said shaft into close proximity of the patient's cystic duct;
   (d) depressing said plunger to advance said hook-shaped needle through the wall of said cystic duct;
   (e) releasing said plunger to clamp the wall of the cystic duct between a portion of said hook-shaped needle and the distal end of said shaft; and
   (f) injecting a contrast fluid through said inner tubular member and said hollow needle into said cystic duct.

* * * * *